United States Patent
Jimenez Onofre

(10) Patent No.: US 11,786,399 B2
(45) Date of Patent: Oct. 17, 2023

(54) PHACO TIPS WITH DISSOCIATION OF THE SUCTION AND ULTRASOUND FUNCTIONS

(71) Applicant: Gabriel Jimenez Onofre, Bogota (CO)

(72) Inventor: Gabriel Jimenez Onofre, Bogota (CO)

( * ) Notice: Subject to any disclaimer, the term of this patent is extended or adjusted under 35 U.S.C. 154(b) by 0 days.

(21) Appl. No.: 16/901,640

(22) Filed: Jun. 15, 2020

(65) Prior Publication Data

US 2020/0306082 A1 Oct. 1, 2020

Related U.S. Application Data

(63) Continuation-in-part of application No. PCT/IB2018/060026, filed on Dec. 13, 2018.

(30) Foreign Application Priority Data

Dec. 15, 2017 (CO) .................. NC2017/0012914

(51) Int. Cl.
*A61F 9/007* (2006.01)

(52) U.S. Cl.
CPC .... *A61F 9/00745* (2013.01); *A61B 2217/005* (2013.01)

(58) Field of Classification Search
CPC ........ A61F 9/00745; A61F 9/00; A61F 9/007; A61B 2217/005; A61B 1/00; A61M 1/00
See application file for complete search history.

(56) References Cited

U.S. PATENT DOCUMENTS

| | | | | |
|---|---|---|---|---|
| 5,163,433 A | * | 11/1992 | Kagawa | A61B 17/22012 604/27 |
| 6,159,175 A | * | 12/2000 | Strukel | A61F 9/00745 604/22 |
| 6,592,541 B1 | * | 7/2003 | Kurwa | A61F 9/00745 604/521 |
| 7,037,296 B2 | | 5/2006 | Kadziauskas et al. | |
| 7,588,553 B2 | | 9/2009 | Dewey | |
| 8,398,578 B1 | | 3/2013 | Zolli | |
| 2009/0247936 A1 | * | 10/2009 | Escaf | A61F 9/00745 604/22 |
| 2013/0226152 A1 | | 8/2013 | Zolli | |
| 2014/0276365 A1 | * | 9/2014 | Koplin | A61M 1/77 604/22 |
| 2015/0005753 A1 | | 1/2015 | Walter | |
| 2017/0007451 A1 | | 1/2017 | Depenbusch | |
| 2019/0298517 A1 | * | 10/2019 | Sanchez | A61F 2/2427 |

* cited by examiner

*Primary Examiner* — Timothy J Neal
*Assistant Examiner* — Andrew P. Restaino
(74) *Attorney, Agent, or Firm* — Hoglund & Pamias, PSC; Roberto J. Rios

(57) ABSTRACT

The present invention discloses a new phacoemulsification tip which can be used during cataract surgery. Particularly, the phacoemulsification tip of the invention physically separates the aspiration function from the ultrasonic energy release point, where the distal region of the tip is blind, and the aspiration port is at a suitable distance from the distal end of the tip of the invention.

5 Claims, 8 Drawing Sheets

PHACO TIPS WITH DISSOCIATION OF THE SUCTION AND ULTRASOUND FUNCTIONS

TECHNICAL FIELD

The present invention belongs to the field of cataract surgery, particularly to the design of the tools used in said surgery by the phacoemulsification technique. More particularly, the present invention relates to the design of phacoemulsification tips that allow surgery to be carried out safely for the patient, by avoiding the common setbacks of said technique, particularly the rupture of the posterior capsule.

BACKGROUND OF THE INVENTION

The human eye, also called the eyeball is the organ responsible for vision. It consists of three layers: the sclerocornea (outer layer), the uvea (middle layer) and the retina (inner layer). Each of these layers contains different portions or structures.

Attached to the uvea and located in the anterior third of the eyeball is a lens called crystalline, which is a transparent structure that acts as a biconvex lens and whose main functions are to refract light towards the retina in the inner layer of the eye and allow to focus correctly objects located at different distances. Said lens is covered by an elastic, thin and transparent capsule called the lens capsule, whose function is to keep the lens in position by fixing it to the uvea. In addition to the capsule, the lens is formed in its interior by cells that are gradually compacted during embryological development and that end up forming the nucleus of the lens (more internal and compact area) and the lens cortex (soft consistency).

The composition of the lens is mostly water and protein. These proteins are distributed in a precise way allowing the lens to remain transparent and light to pass through it.

For different reasons, but mainly with age, some of the proteins accumulate and begin to cloud or opacify part of the lens, decreasing the light that reaches the retina. Such opacification commonly occurs in the cortex or nucleus, but rarely in the lens capsule. This opacification of the lens is called a cataract. A lens with cataract not only loses its transparency but also changes its consistency and increases its hardness, thus, as the cataract progresses, the hardness of the same increases.

Studies have shown that cataract is the leading cause of vision loss in people over 45 years. In addition, it is one of the most common eye diseases in people around the world.

Nowadays the only possible and effective treatment to eliminate the cataract is surgery that removes the part of the lens that is opaque, keeping the lens capsule intact, and then using it as a "pocket", in order to introduce and maintain the lens that will replace the removed lens.

In other words, cataract surgery removes the natural (crystalline) lens that has been opacified and replaces it with a synthetic intraocular lens, all within the lens capsule that remains intact.

The surgery most commonly used to remove the cataract currently is extracapsular lens extraction, a term that refers to keeping the lens capsule in position, and then using it as a support for the synthetic intraocular lens. This surgery at the same time can be performed in 2 ways: The technique known as extracapsular extraction (EECC) that involves removing the entire lens (lens), for which it is necessary to make an incision in the eye of the lens' size (about 10 mm), and the technique known as phacoemulsification (PHACO).

Both surgeries perform an opening in the lens capsule, in its anterior portion where the opaque lens is removed and then the remaining portion of said capsule is used as a support for a synthetic intraocular lens.

Unlike EECC, phacoemulsification cataract surgery is a procedure in which the natural (crystalline) lens, which is opaque by a cataract, is fragmented by the use of ultrasound, and subsequently suctioned (aspirated) to remove the cataract This allows said extraction to be done through a very small incision, thus the use of sutures is reduced to a maximum of 1 point. All together allows cataract surgery by phacoemulsification to be less traumatic, since the wound heals faster and patients can resume normal activity more quickly compared to conventional cataract surgery (EECC) and with less need for use post-surgery optical correction.

In more detail, phacoemulsification is carried out through a series of steps, which must be performed skillfully to avoid complications during surgery. These steps are: i) Application of eye drops to dilate the pupil, ii) Application of anesthesia; iii) Cleaning the eye with antiseptic; iv) Opening of the eyelids and exposure of the eyeball; v) Entry into the eye through one or two auxiliary micro-incisions of less than 1 mm and a main micro-incision (2.2 mm); vi) Viscoelastic injection, a thick substance of gelatinous consistency that maintains the shape and pressure of the eyeball during surgery; vii) Continuous circular capsulorhexis, through which a circular opening of approximately 5.5 mm is created in the anterior lens capsule (cataract), and where this opening gives the surgeon access to the cataract; viii) Hydrodissection, where fluid is injected between the cataract and the capsule, which loosens and separates the opaque lens from the capsule; ix) Fragmentation of the cataract into smaller pieces, which allows the fragments to be discarded and taken to the center of the eye to move them away from the posterior capsule, avoiding breaking it. This fragmentation is carried out with the help of the phacoemulsifier which, by means of a special handpiece, generates a vibration at ultrasound frequencies which are transmitted to the eye through a phaco tip; x) Phacoemulsification and aspiration of the smallest fragments of the cataract to be removed. This is also done with the help of the same handpiece and phaco tip; xi) Exchange of the handpiece with an irrigation-aspiration piece, which achieves the aspiration of all cortical remains by carefully detaching them from the capsule; xii) Implantation of the intraocular lens inside the capsular sac, where the integral capsular sac is what allows the implantation of the intraocular lens in the ideal place for it to function; xiii) Placement of 1 point in the main incision; xiv) Aspiration of the remaining viscoelastic; xv) Hydration of auxiliary incisions so that they remain hermetic.

To perform cataract surgery by phacoemulsification, a device called phacoemulsifier is used in stage ix) and x) of the process described above. This device has four main components.

First, an irrigation system which in its simplest version is a bottle that hangs at varying heights above the eye to allow the infusion of liquid.

Second, a foot-controlled pedal, which allows the surgeon to control the device, having a series of positions that determine the process to be carried out.

Third, an ultrasound handpiece that has a distal device, similar to a needle, commonly known as a phaco tip, and that is located at the distal end of said handpiece. This phaco tip is responsible for transmitting the ultrasound energy, since the tip vibrates longitudinally and from back to front, between 30,000 and 60,000 times per second (30 to 60 kHz). Recently, devices of this type that generate torsional movements have also been developed. Additionally, said phaco tip is hollow and has an opening or suction port that sucks and removes the emulsified material, which is the result of contact between the moving tip and the lens.

Fourth, a pump, which through a suction line allows to extract fluids and the remains of the phacoemulsified lens through said port.

There are different techniques for phacoemulsification that include multiple options for the phacoemulsifier, for the procedure itself, and especially for the different phases of surgery. These options include solutions for handling complicated situations, such as new viscoelastic substances, various designs of foldable intraocular lenses, devices to improve phacoemulsification (phacolaser, clamps for splitting the core, vacuum control mechanisms, etc.), as well as options of phaco machines that come equipped with software that allows modifying the parameters of the machine according to the type of cataract that the patient has and even allows modifying the parameters of the machine during the different phases of the same procedure.

That is to say, the surgeon can choose, depending on the patient or according to the stage of the surgery in which he or she is, to irrigate the eye in order to maintain its pressure, irrigate and aspirate, or irrigate, aspirate and also do phacoemulsification.

For example, in some cases and depending on the type of cataract, the surgeon may use an aspiration tip that does not generate ultrasound for the sole purpose of aspirating. This may be the case of surgery in a child or young patient in which the lens is extremely soft. For the use of the aspiration tip it is not necessary to use a handpiece for phacoemulsification but only a handpiece that performs aspiration. This aspiration without phacoemulsification is also indicated in the toughest cataract surgeries once the cataract has been removed by phacoemulsification and it is desired to remove the softer remains that remain attached to the lens capsule. There are records of aspiration tips that may include cutting systems that help decrease lens fragments.

Of all the components of the phacoemulsifier, the phaco tip has one of the most important roles in phacoemulsification cataract surgery, since it is responsible for transmitting ultrasound energy, which thanks to the vibration generated at the phaco tip produces a phenomenon called cavitation that consists of a "microexplosion" of the tissues, which emulsifies the lens material. This phenomenon of cavitation and phacoemulsification is what allows "cutting" or fragmenting the lens into smaller pieces to properly manipulate them and then emulsify them in their entirety allowing their subsequent extraction by aspiration.

Despite the great advances in cataract surgery, the phaco equipment and all its components have presented improvements focused mainly on two aspects. The first is to reduce the size of the incisions, achieving better results. The second, technological advances in surgery have focused on improving the safety of the procedure, being particularly important to keep the posterior lens capsule intact since this is the support of the artificial intraocular lens that is placed during surgery. The above taking into account that if it is not possible to place an intraocular lens that replaces the opaque natural lens (the cataract), the patient's vision cannot be restored.

These improvements in security have focused on optimizing the different aspects of the components of phacoemulsification machines. In this way, important advances have been observed in the phaco and suction parts, in the pumps and all their components including software that very precisely handle the suction pressure and the vacuum, and even in the irrigation systems used.

Since the beginning of the procedure 50 years ago, the phaco tips have undergone very few modifications maintaining the original principle. This differs totally from the evolution that the rest of the components of the phacoemulsification machines have had, which have had surprising technological developments. In this way, there is a need to design improved phaco tips, especially considering that any change in the shape or size of the tip directly affects the performance of phacoemulsification cataract surgery.

At present, the most frequently used phaco tips consist of hollow cylindrical structures with a distal bevel or oval end (typical needle shape) and sharp edges. This form has been maintained thanks to the belief that for a proper phacoemulsification of the crystalline lens, in addition to ultrasound with its cavitation effect, a sharp object that facilitates its fragmentation is required.

Additionally, the current phaco tips have a suction port housed in front of the tip (front or front or distal part). Said suction port has two uses: i) the suction of the opaque lens, which is attracted to the tip, and is fixed and secured thanks to a vacuum effect, preventing it from escaping during the process, so that the cataract remains direct contact with the phaco tip allowing it to be emulsified with ultrasound. And ii), the aspiration and elimination of the emulsified lens with ultrasound, which completely eliminates the use of the aforementioned "sharp aspiration tips". It has also been found that a large suction port increases the suction capacity and therefore decreases the operation time.

Despite the great advances in phacoemulsification machines, mainly focused on improving the effectiveness of ultrasound with less transfer of it to the eye (phenomenon that inflames, delays or puts at risk the recovery of vision), in improving the fluidics of the system (avoiding eye collapses in the aspiration phases), or in smaller incisions, there is still a significant probability of complications.

For example, the cut that is produced thanks to the edge and angle of the phaco tips, together with their mechanical movement, can cause significant damage to the lens capsule and even adjacent structures, which creates a serious safety problem for the patient.

Additionally, the current phacoemulsification technique, as well as the tips used during said procedure, necessarily generate a vacuum (suction) in the suction port located on the distal front of the tip, in order to attract and hold the lens towards the tip to then be emulsified and aspirated. During this step of process, the port of the phaco tip became occluded by crystalline fragments, resulting in an increased negative pressure within the system (particularly the disposal ducts or hoses), that ends when the port became unoccupied. As a result, the internal negative pressure produces a sudden increase in the flow of liquid of the eye which allows a partial collapse of the eye as the differences in the internal and external pressures are compensated, this sudden collapse is known as surge.

Moreover, when the suction is generated, not only the lens is attracted, but any other structure of the eye can become trapped in the tip, causing serious complications in the surgery. For example, when the posterior capsule of the lens is trapped while the suction process or the surge is taking place, it could break; If the rupture is large enough, there is a risk of not being able to place an intraocular lens during the procedure, which leads to the abortion of the surgery, and the patient must be referred to a retinologist for a different lens to be placed that does not require the capsule holder. This generates clinical risks and high costs, which lead to the rupture of the lens capsule being the greatest fear of every cataract surgeon.

When a posterior capsular rupture occurs, the anterior part of the eye (anterior chamber) is communicated with the posterior part of the eye (posterior chamber). The posterior chamber of the eye is occupied by a gelatinous substance called the vitreous humor. When the 2 chambers are communicated, the vitreous humor moves previously occupying the spaces of the anterior chamber, not allowing the surgery to be completed successfully. This obliges to perform an additional procedure known as vitrectomy, with the underlying risks and costs, forcing in many cases to defer the placement of the intraocular lens through a new intervention. Furthermore, it has been observed that the possibility of rupture of the capsule by suction is increased in the phaco tips where the aspiration port is very large.

Now, since the early stages of the development of this technique the aforementioned risks have been identified, so that to date there are developments focused on reducing the possibility of complications. The main developments have focused on the phacoemulsification machines already mentioned, and although the design of the tips is similar to that of the tips used since the beginning of the phaco, variations have been described that seek to optimize the function of the tips or improve their safety.

With respect to the cutting effect of the current phaco tips, U.S. Pat. No. 5,213,569A proposes phaco tips with distal edges with modified angles that seek to improve the efficiency of ultrasound by decreasing the energy used. In addition, said phaco tips have rounded edges to reduce the risk of inadvertent damage to the eye tissue.

For its part, U.S. Pat. No. 7,588,553B2 discloses a phaco tip that has a rounded outer edge and inner edge to eliminate any sharp edges, and thus ensure that the needle can be used to deliver ultrasonic energy, to emulsify unwanted tissue and to aspirate said tissue through the suction port, without using sharp surfaces to cut. This document mentions that the rounded outer and inner edges of the end of the reported phaco tip increase the safety of the surgical procedure by reducing the risk of damage to the capsule or other intraocular structures or tissues near the surgical site.

Likewise, U.S. Pat. No. 7,037,296B2 discloses a multipurpose tip which can be used both in the phacoemulsification phase of the cataract by ultrasound and in the aspiration irrigation phase to aspirate the cortex or to polish the posterior capsule. This tip has a configuration where the distal end of said tip has a flat top surface on which the suction port is located. The lower distal end is not flat but rounded which prevents sharp edges. This is how this characteristic suggests that there is no sharp edge at the distal end of the tip which avoids complications.

On the other hand, with respect to the risk of rupture of the lens capsule due to the suction generated by the suction port located in the anterior part of the tip, the anteriority U.S. Pat. No. 8,398,578B1 mentions that the use of conventional phacoemulsification tips that are sharp and that have an excessively large suction port presents a high risk of causing ruptures of the lens capsule. Therefore, this document discloses "capsule-friendly" tips suitable for use with phacoemulsification machines, which are intended to safely eliminate cataracts without sucking the iris tissue or thereby pulling and breaking the capsule. Said "capsule-friendly" tips are constructed so that they are rounded with multiple small pores on the anterior surface or incorporate a front shield that prevents aspiration through the extremely large suction port.

Additionally, the state of the art discloses different aspiration ports, present in specialized devices only for the cataract aspiration stage, in order to remove the cortical remains of the cataract and separate them from the lens capsule, after performing the phacoemulsification. That is to say, they are useful for processes where one tip is used to phacoemulsify and another tip to aspirate. In this regard, for example, document US20150005753 discloses a tip for aspiration in cataract surgery that is round, has blunt edges and a port at some distance from the front of the tip, which also allows cutting, fragmenting or reducing the lens fragment size.

Other tips have been described that seek to improve their efficiency without taking into account the safety aspect thereof as in US20170007451A1 and in U.S. Pat. No. 8,992,459B2.

From all the above, it is clear that in the prior art state rounded phaco tips were known to avoid cuts due to sharp and angled tips. In addition, the implementation of suction ports other than those known that attempt to solve the risk of rupture of the lens capsule is also known.

However, surgeons continue to fight the safety problems caused by cataract surgery. The current phaco tips continue to damage the structures of the eye and at the same time continue to trap and break the lens capsule due to suction, which, therefore, remains the biggest drawback in cataract surgery.

The above is the result of the broad acceptance of two principles: i) that for proper phacoemulsification it is necessary to have an aspiration linked to the site of contact with the lens, which in theory allows obtaining a cutting effect and emulsifying the lens as a result of cavitation effect thereof, and ii) that the aforementioned aspiration allows the lens to be held for proper handling. In this way, there is a prejudice according to which it is assumed that the lack of this lens aspiration functionality in the phaco tips does not allow the procedure to be carried out successfully.

Consequently, despite what has been disclosed in the state of the art, there is still a need for new and improved phaco tips that include all the features necessary to carry out the ultrasonic emulsification process and that completely eliminate the safety problems outlined above.

SUMMARY OF THE INVENTION

In accordance with the teachings of the prior art and taking into account the existing technical needs, it is the object of this application to provide a new phaco tip which can be used, in cataract surgery during lens phacoemulsification, or in the later phase in which the cortex lens is aspirated, when it is necessary to emit ultrasound in case the masses require it due to their hardness.

The phaco tip for cataract surgery of the invention is characterized by separating the two main functions of the phaco tips designed so far, that is, the phacoemulsification tip of the invention physically separates the aspiration function from the release point of the ultrasonic energy This is achieved by designing a blind phaco tip, where the blind phaco tip consists of a proximal portion that is the one that connects to the phaco handpiece, a blind distal portion, which is responsible for the release of the ultrasonic energy and a suction port located at an intermediate point between the distal and the proximal part. This arrangement achieves a complete dissociation of the functions of aspiration and ultrasound.

The unique design of the phaco tip of the invention makes it possible to perform a phacoemulsification of the lens and suction of the mass in a safer way, since the aspiration port is not at the end of the distal end, as is known in the state of the art, but at an intermediate point between the distal and the proximal part of the phaco tip, so that the lens capsule is protected and it is prevented from being trapped in the aspiration port and broken. This modification allows to improve the results in cataract surgery since it increases the safety of the procedure.

Thus, the device for cataract surgery of the invention described herein provides a novel alternative to those known in the state of the art, since it consists of a phacoemulsification tip whose main characteristic is to separate the portion of the tip that emits ultrasound with the portion of the tip that is responsible for aspiration, with the sole purpose of protecting the lens capsule.

DETAILED DESCRIPTION OF THE INVENTION

Figure 1:
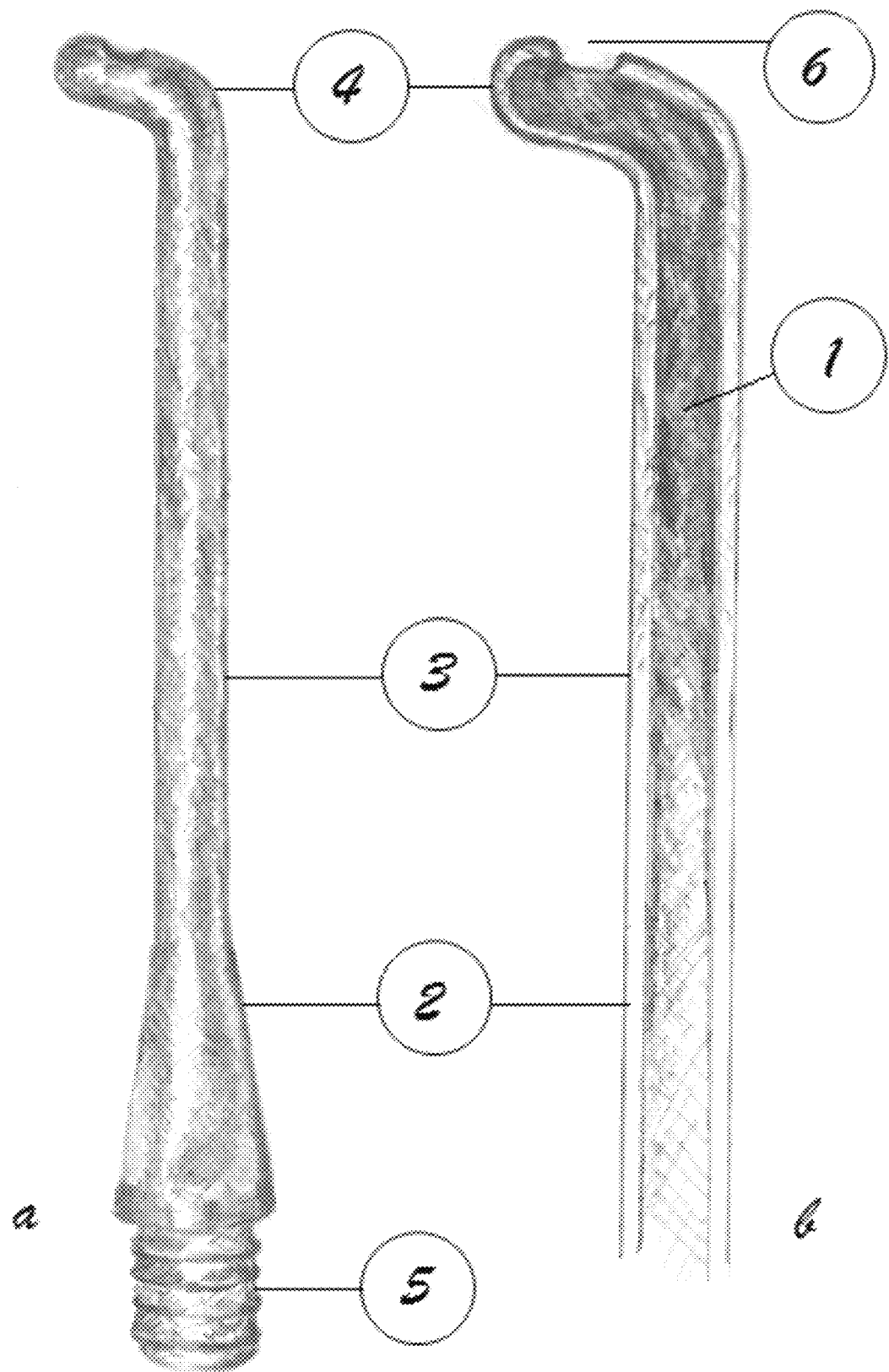
FIG. 1 shows (a) a side view and (b) a longitudinal section view of a particular embodiment of the tip of the invention.

In accordance with FIG. 1 (a), the blind tip for phacoemulsification of the invention consists of a hollow cylinder (1) consisting of a proximal portion (2) that can be attached to a handpiece of a phacoemulsification equipment, a middle body (3) and a distal portion (4).

The hollow cylinder (1) comprises an inner diameter and an outer diameter as shown in FIG. 1 (b), which may vary in proportion without altering the function of the blind tip for phacoemulsification.

The hollow cylinder (1) comprises a proximal portion (2), which in turn consists of a thread (5) for screwing the hollow cylinder (1) into the handpiece of a phacoemulsification equipment (not shown), so that the hollow part of the hollow cylinder (1) continues in the suction system of the handpiece. Where the handpiece is responsible for the vibration of the distal portion (4) of the tip, both in its rotation, and in the anteroposterior movement, at the frequencies determined by the user.

The hollow cylinder (1) further comprises a middle body (3) this being the middle part of the hollow cylinder (1) and which communicates the proximal portion (2) and the distal portion of the phaco tip (4).

Figure 3:
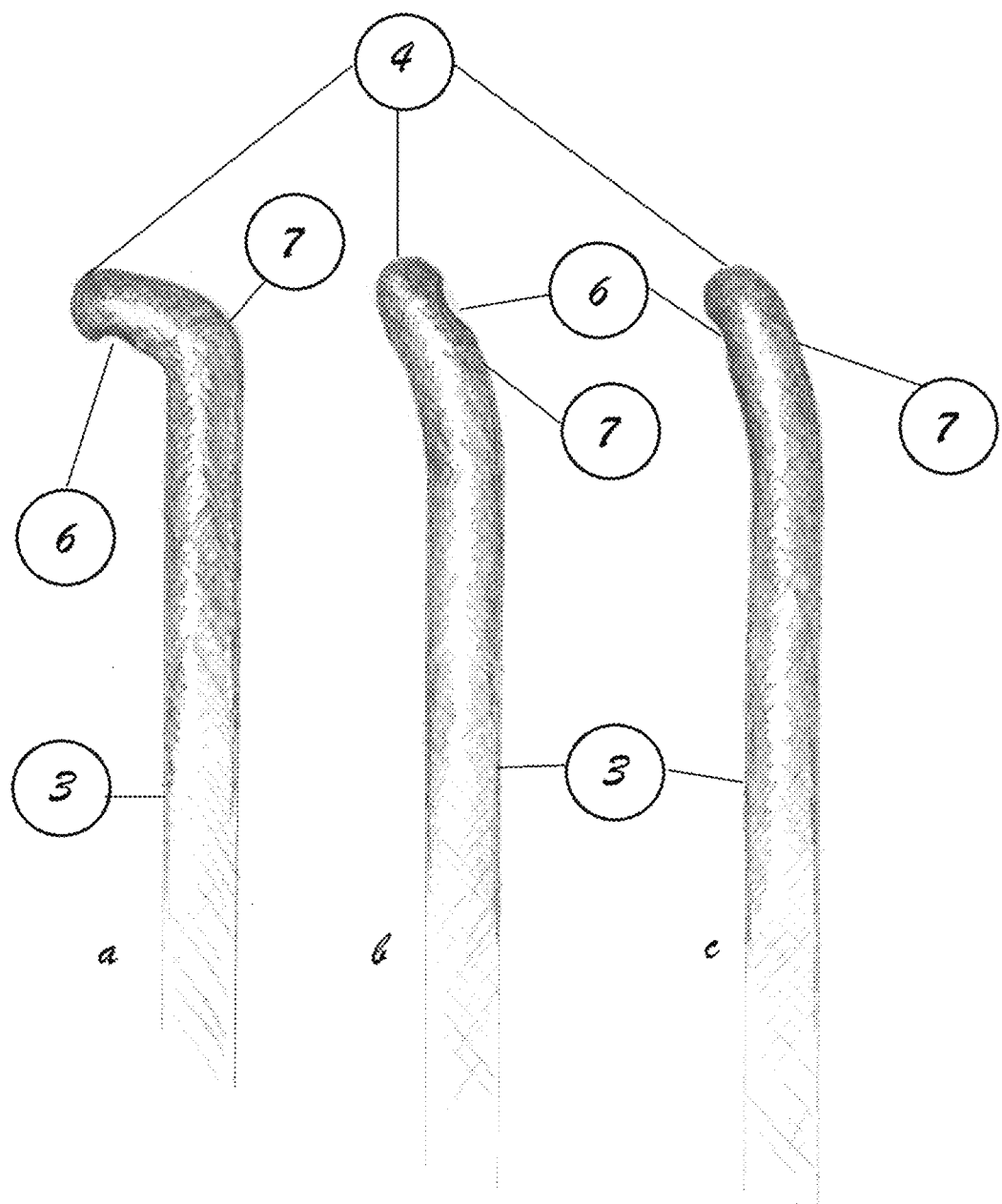
FIG. 3 shows three preferred embodiments of the invention, in which the location of the suction port (6) and the angle (7) formed by the middle body (3) and the distal portion (4) are illustrated.

The middle body (3) joins the distal portion (4) forming an angle (7) that can vary between 0 and 70°, preferably between 15 and 20°, as illustrated in FIG. 3.

Additionally, the hollow cylinder (1) comprises a distal portion (4) whose main characteristic is to be blind, in a manner that the hollow cylinder (1) extends from the handpiece connected to the aspiration system to an end that does not communicate with the outside.

The distal portion (4) of the phacoemulsification tip may vary, as long as it meets the criteria of being a blind end. For example, the distal portion (4) may have a rounded convex shape, without cutting or sharp edges as illustrated in FIG. 1, where said structural characteristic is intended to protect the posterior capsule from unwanted rupture.

Figure 4:
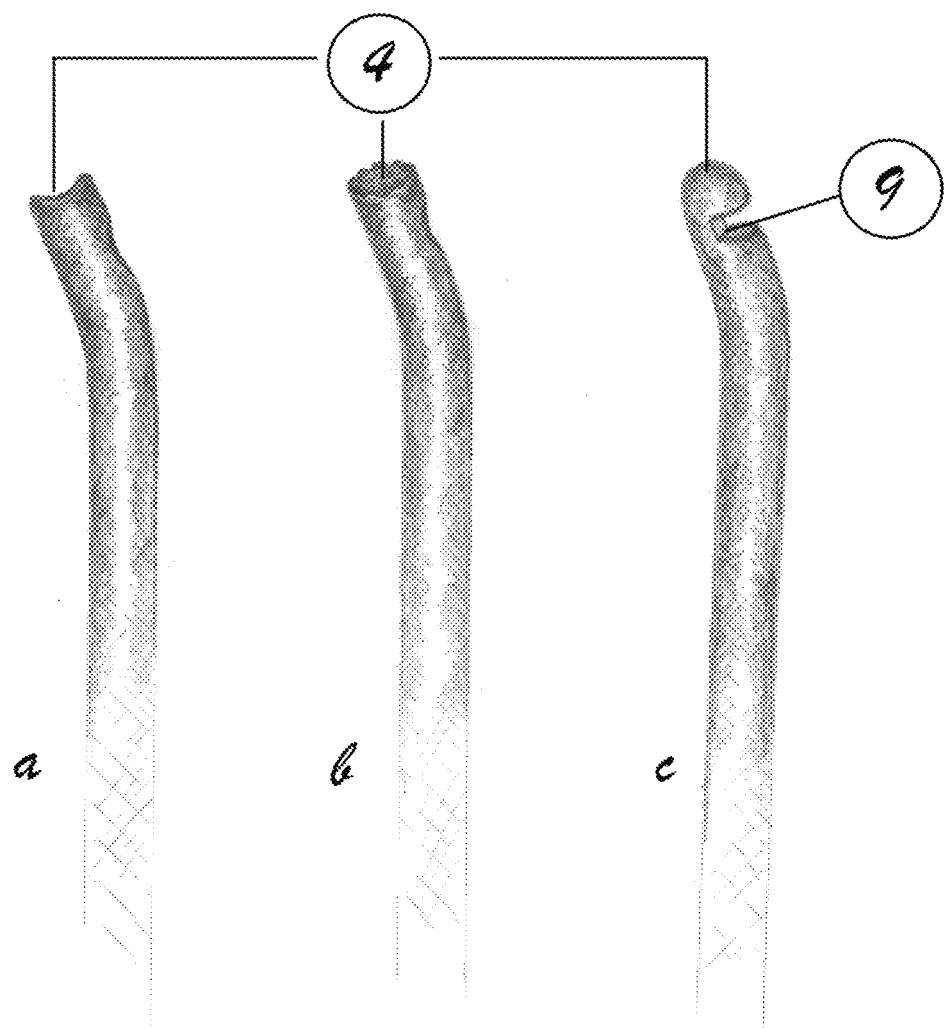
FIG. 4 shows three preferred embodiments of the invention in which multiple termination options are illustrated the distal portion (4) of the phaco tip.

Alternatively, the blind distal portion (4) may have a concave shape with non-sharp edges, as illustrated in FIG. 4 (a). In another preferred embodiment, the blind distal portion (4) may have wavy non-sharp edges as in FIG. 4 (b).

A particular embodiment of the phaco tip of the invention comprises a blind distal portion (4) comprising a groove (9) that encompasses a percentage of the tip as illustrated in FIG. 4 (c).

Figure 2:
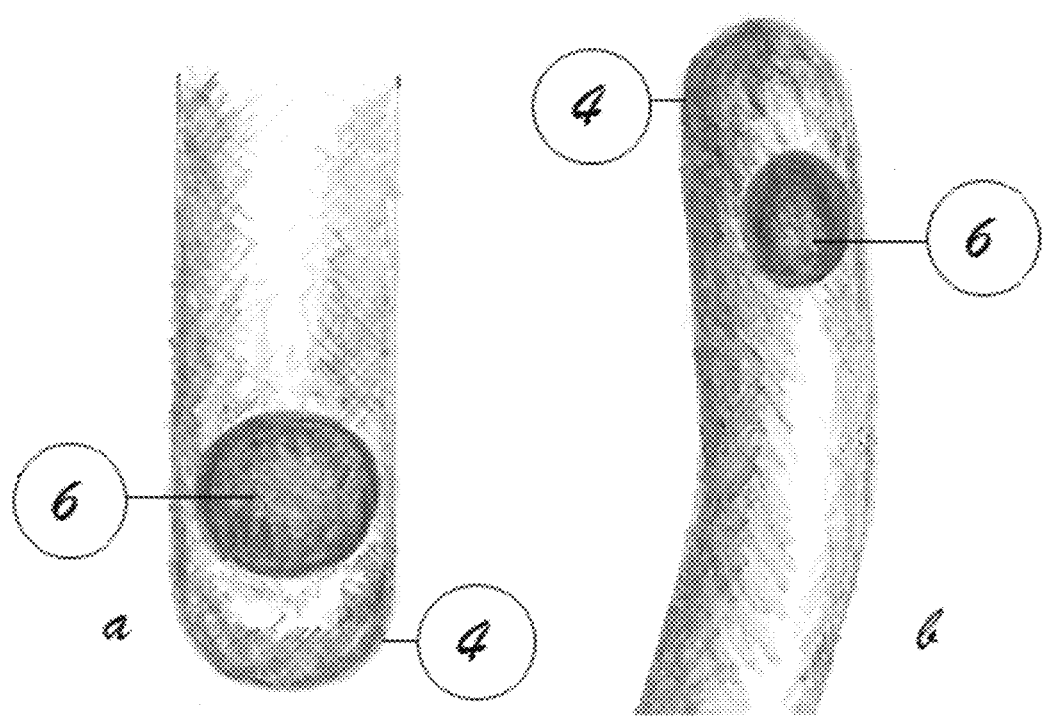
FIG. 2 shows (a) an anterior view and (b) an anterior perspective view of the phaco tip of the invention.

Finally, the hollow cylinder (1) comprises a suction port (6), which is located in the hollow cylinder (1), at a suitable distance from the distal end (4) of the tip of the invention as shown in the FIGS. 2 (a) and (b).

Figure 5:
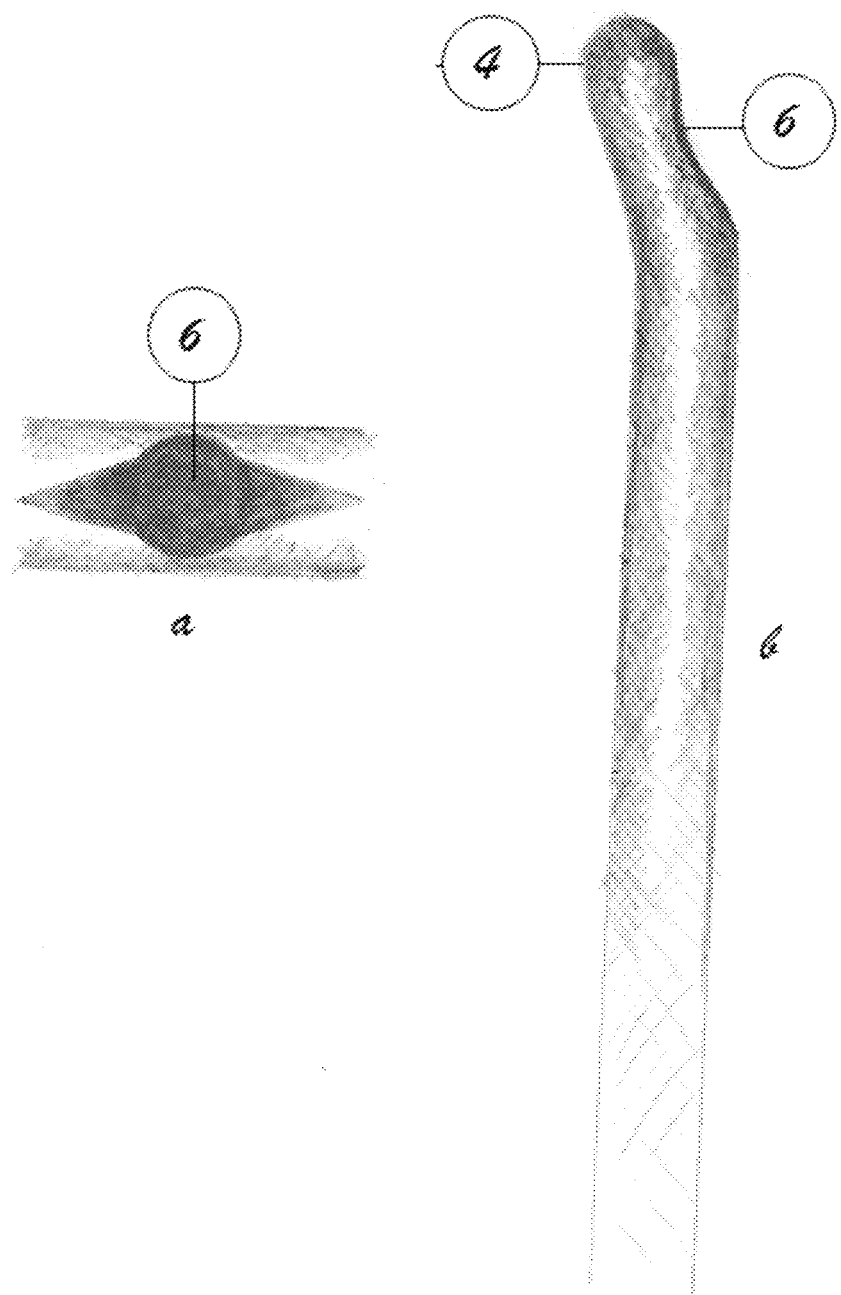
FIG. 5 shows a particular embodiment of the invention in which the aspiration port (6) of the phaco tip is shaped like a rhombus.

The diameter of the aspiration port (6) can vary without compromising the objective of the invention, but it is intended to be as large as possible to optimize the suction function. According to FIG. 2 (a), in a particular embodiment, suction port (6) covers the entire internal diameter of the hollow cylinder (1). In another particular embodiment, the suction port (6) comprises alternative shapes to the circular, such as an oval shape or a rhombus shape as illustrated in FIG. 5.

Now, the aspiration port (6) can be located at different sites of the distal portion (4). FIG. 3 illustrates three particular embodiments of the phaco tip of the invention, wherein the aspiration port (6) is located at the posterior part of the distal portion (4) (FIGS. 3a and 3c) or wherein the aspiration port (6) is located in the anterior part of the distal portion (4) (FIG. 3b).

In particular embodiments, the phacoemulsification tip of the invention may include more than one aspiration ports (6). In a preferred embodiment, the phacoemulsification tip of the invention comprises two aspiration ports located on each side of the distal portion (4).

Figure 6:
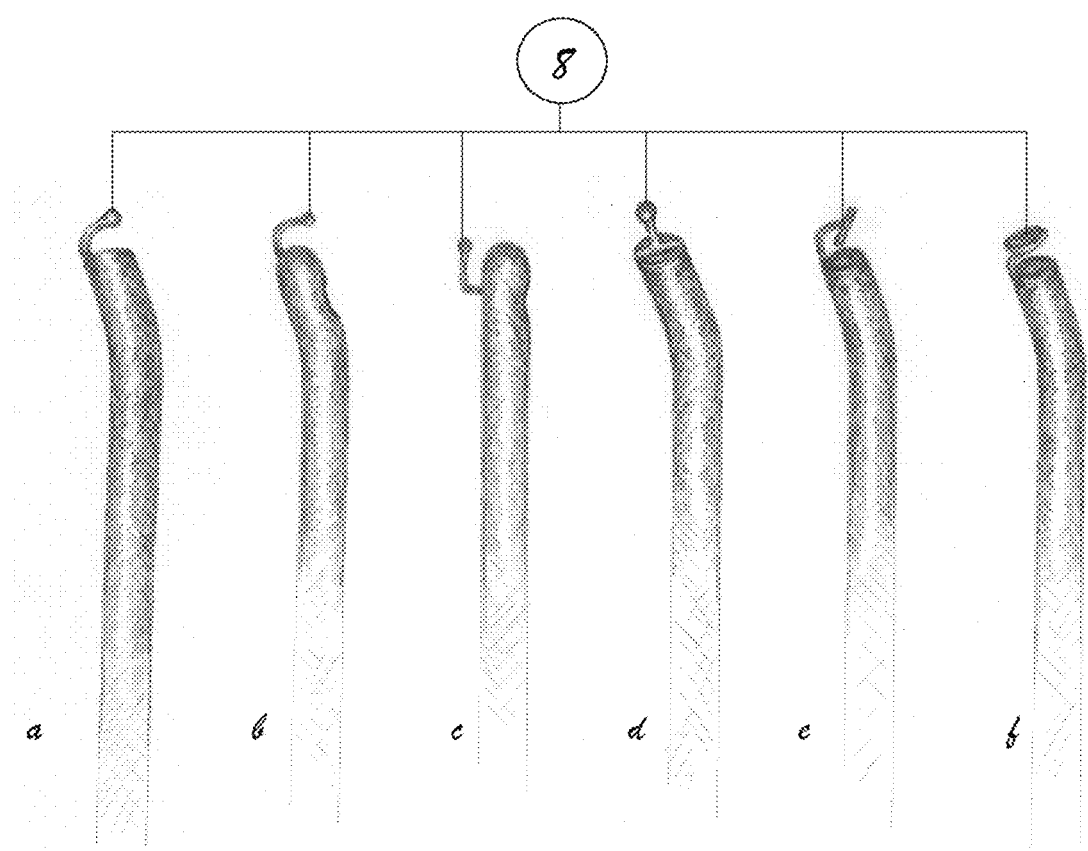
FIG. 6 shows particular embodiments of the invention comprising an extension (8) at the distal end (4) of the phaco tip.

Alternatively, and in order to physically separate the distal portion (4) in charge of the aspiration port (6), the phaco tip of the invention comprises at the distal end (4) an extension (8) ending in a rounded structure as illustrated in FIG. 6. This structure is responsible for releasing the ultrasound, and it also serves as a barrier so that the capsule cannot get trapped in the suction port. In particular, FIG. 6 (c) illustrates a preferred embodiment for phaco tips that do not have the angle (7), said design optimizes rotational ultrasound at said straight tips, in which only longitudinal ultrasound works.

Figure 7:
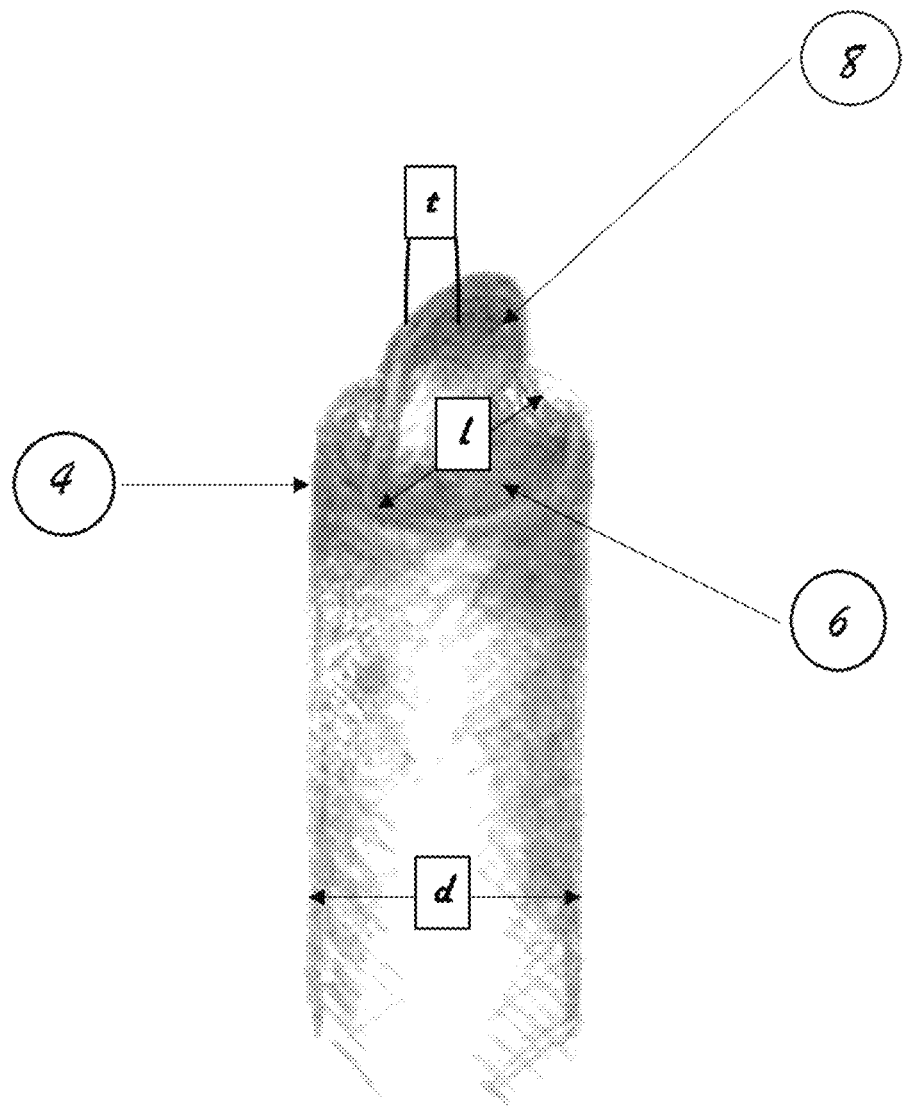
FIG. 7 shows a particular embodiment of the invention wherein the extension (8) is shaped as a flat plate that divides the aspiration port (6) in at least two portions.

In another preferred embodiment illustrated in FIG. 7, the extension (8) is shaped like a flat plate, which is expanded from the tip of the distal portion (4) wherein the aspiration port (6) is located at. In this way, the extension (8) forms a wall that divides the aspiration port (6) into at least two portions. This arrangement allows the suction of the crystalline fragments to be carried out at one side of the aspiration port (6). Therefore, the occlusion of the port is given at only one side while the other side allows the entry of liquid compensating the negative pressure caused by the occlusion, avoiding the surge and increasing the overall safety of the procedure.

In an even more preferred embodiment of the invention, the plate-shaped extension (8), has a length (I) that is approximately equal to the diameter (d) of the hollow cylinder (1) and a thickness (t) that is substantially smaller than the diameter (d).

The hollow cylinder (1) can be manufactured in any material known in the art that has the characteristics required for its function, which is to vibrate at the determined frequencies so that the required ultrasonic energy is released.

In a preferred embodiment the phacoemulsification tip of the invention is fabricated in titanium or similar metallic materials. In other embodiments phacoemulsification tip of the invention is made of a medical grade silicone or similar materials. In additional embodiments the phacoemulsification tip of the invention is fabricated with a combination of different materials.

In additional embodiments, the phacoemulsification tip of the invention may be employed in association with other elements commonly used for cataract surgery, i.e. as sleeves, sheaths or covers fabricated in different materials such as medical grade silicone or the like.

Figure 8:
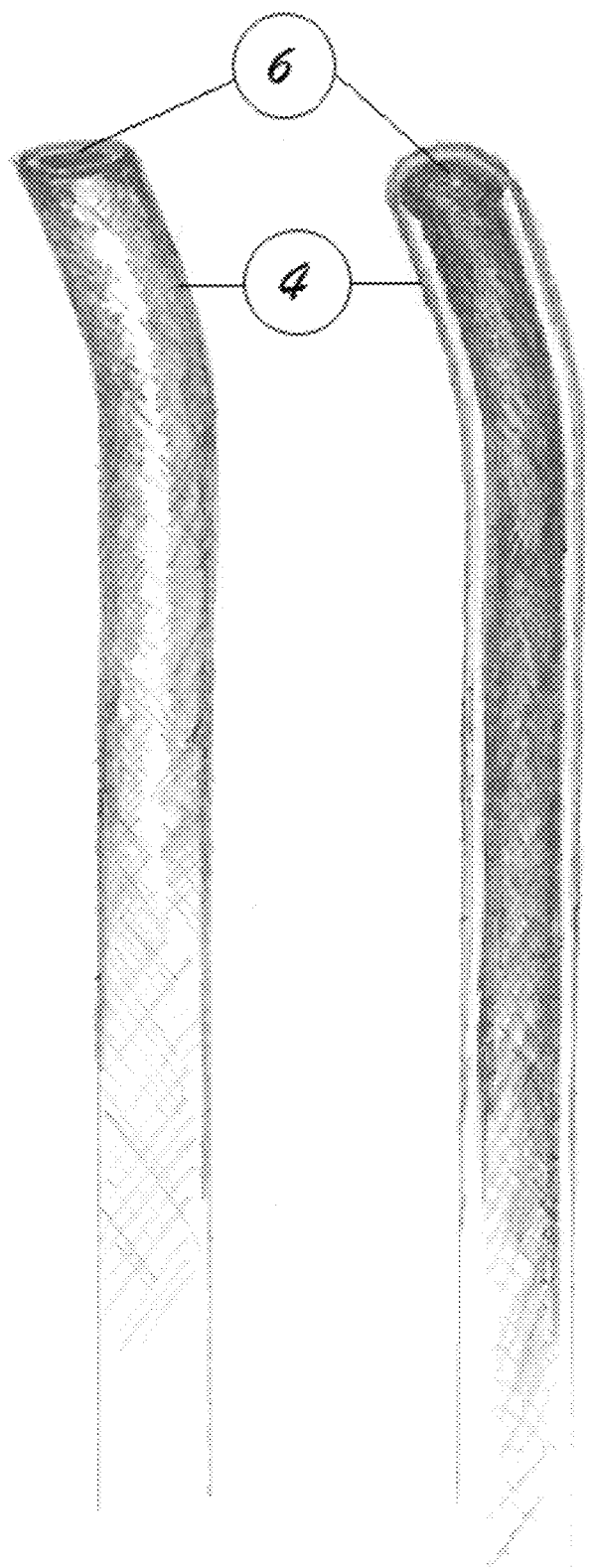
FIG. 8 shows the general structure of the phaco tips known in the state of the art prior to the invention.

Thus, the present invention provides a blind phacoemulsification tip that allows the distal portion (4) and its vibration function to be separated from the aspiration port (6), which differentiate it from the tips already known in the state of the art, which have a suction port (6) at the tip of the distal portion (4) as illustrated in FIG. 8.

Finally, it should be understood that the variations or secondary modifications made to the particular phacoemulsification tip that has been disclosed in the present application are within the scope of the present invention.

What is claimed is:

1. A tip for phacoemulsification formed by a hollow cylindrical body which in turn consists of:
    a proximal portion, configured to be joined to a handpiece of a phacoemulsification equipment;
    a middle body;
    a distal portion;
    an elongated extension extending from the distal portion, having a diameter that is uniform and smaller than the diameter of the distal portion and a spherical, cylindrical, or rounded three-dimensional structure located at a free end of the elongated extension, wherein said structure acts as an ultrasonic energy release point separated from the distal portion by said elongated extension, and wherein said structure serves as a barrier so that the lens capsule cannot get trapped in an aspiration port; and
    the aspiration port separated from the elongated extension and not forming part of the elongated extension.

2. The tip for phacoemulsification of claim 1, wherein the proximal portion comprises a thread for screwing the hollow cylindrical body into the handpiece of a phacoemulsification equipment, such that the hollow part of the hollow cylindrical body continues in the handpiece.

3. The tip for phacoemulsification of claim 1, wherein the distal portion forms an angle with respect to said middle body varying between 0 and 70°.

4. A tip for phacoemulsification formed by a hollow cylindrical body which in turn consists of:
    a proximal portion, configured to be joined to a handpiece of a phacoemulsification equipment;
    a middle body;
    a distal portion comprising an aspiration port at the end of the distal portion; and
    a plate-shaped extension positioned over said aspiration port and expanding away from said aspiration port, forming a wall that divides the aspiration port into at least two portions that are parallelly-oriented throughout their entire length, and wherein said extension acts as an ultrasonic energy release point.

5. The tip for phacoemulsification of claim 4, wherein the plate-shaped extension has a width that is approximately equal to the diameter of the hollow body and a thickness that is smaller than the diameter.

\* \* \* \* \*